US006825232B2

(12) United States Patent
Gamache

(10) Patent No.: US 6,825,232 B2
(45) Date of Patent: Nov. 30, 2004

(54) USE OF HYDROXYEICOSATETRAENOIC ACID COMPOUNDS TO TREAT OPHTHALMIC INFLAMMATORY DISORDERS

(75) Inventor: Daniel A. Gamache, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 37 days.

(21) Appl. No.: 10/409,730

(22) Filed: Apr. 9, 2003

(65) Prior Publication Data

US 2003/0236307 A1 Dec. 25, 2003

Related U.S. Application Data

(60) Provisional application No. 60/389,115, filed on Jun. 14, 2002.

(51) Int. Cl.$^7$ .................. A61K 31/215; A61K 31/19
(52) U.S. Cl. ............................ 514/530; 514/573
(58) Field of Search ......................... 514/530, 573

(56) References Cited

U.S. PATENT DOCUMENTS

| | | | |
|---|---|---|---|
| 4,906,467 A | 3/1990 | Schwartzman et al. | 424/80 |
| 5,102,670 A | 4/1992 | Abraham et al. | 424/650 |
| 5,681,854 A | 10/1997 | Pang et al. | 514/557 |
| 5,696,166 A | 12/1997 | Yanni et al. | 514/573 |
| 6,174,914 B1 | 1/2001 | Yanni et al. | 514/450 |
| 6,255,343 B1 | 7/2001 | Belanger | 514/552 |
| 6,281,192 B1 | 8/2001 | Leahy et al. | 514/8 |
| 6,320,062 B1 | 11/2001 | Belanger | 552/10 |
| 6,326,499 B1 | 12/2001 | Belanger | 548/252 |
| 6,331,566 B1 | 12/2001 | Conrow et al. | 514/549 |
| 6,331,644 B1 | 12/2001 | Klimko et al. | 554/219 |
| 6,342,525 B1 | 1/2002 | Klimko et al. | 514/532 |
| 6,348,496 B1 | 2/2002 | Belanger | 514/560 |
| 6,353,012 B1 | 3/2002 | Hellberg et al. | 514/381 |
| 6,353,022 B1 | 3/2002 | Schneider et al. | 514/530 |
| 6,353,032 B1 | 3/2002 | Graff et al. | 514/912 |
| 6,376,688 B1 | 4/2002 | Ferrante et al. | 554/101 |
| 6,429,227 B1 | 8/2002 | Schneider et al. | 514/530 |
| 6,436,994 B2 | 8/2002 | Conrow et al. | 514/549 |
| 6,437,160 B1 | 8/2002 | Klimko et al. | 554/219 |
| 6,441,035 B2 | 8/2002 | Conrow et al. | 514/549 |
| 6,458,853 B2 | 10/2002 | Graff et al. | 514/912 |
| 6,458,854 B2 | 10/2002 | Graff et al. | 514/912 |
| 6,462,061 B1 | 10/2002 | Belanger | 514/381 |
| 6,552,084 B2 | 4/2003 | Klimko et al. | 514/568 |
| 2002/0077358 A1 * | 6/2002 | Yanni et al. | 514/549 |

FOREIGN PATENT DOCUMENTS

| | | |
|---|---|---|
| CA | 1 251 736 | 3/1989 |
| EP | 0 097 059 A2 | 12/1983 |
| EP | 0 132 089 A1 | 1/1985 |
| WO | WO 92/04905 | 4/1992 |
| WO | WO 96/11908 | 4/1996 |
| WO | WO 99/43310 | 9/1999 |
| WO | WO 00/03705 | 1/2000 |
| WO | WO 00/53198 | 9/2000 |
| WO | WO 01/34549 | 5/2001 |

OTHER PUBLICATIONS

Aldigier et al., "NZB/NZW F1 Mouse Nephritis and Immune Response are Not Changed by Treatment with a 15–Lipoxygenase Derivative," *Prostaglandins Leukotrienes and Essential Fatty Acids*, vol. 47, pp. 159–164 (1992).

Alpert et al., "15–HETE–substituted diglycerides selectively regulate PKC isotypes in human tracheal epithelial cells," *American J. of Physiology*, vol. 277 (3), pp. 457–464 (1999).

Badr, "15–Lipoxygenase Products as Leukotriene Antagonists: Therapeutic Potential in Glomerulonephritis," *Kidney International*, vol. 42 (Suppl. 38), pp. S–101–108 (1992).

Badr, "Lipoxygenases as Therapeutic Targets in the Acute and Subactue Phases of Glomerular Immune Injury," *Progression of Chronic Renal Diseases, Contrib Nephrol.*, vol. 118, pp. 113–125 (1998).

Buchanan et al., "Effects of 13–Hode and Other Momohydroxides on Integrin/Ligand Binding: Implications for Cell Interactions," *Adv. Exp. Med. Biology*, vol. 433, pp. 265–269 (1997).

Camp et al., Inhibition of ionophore–stimulated leukotriene $B_4$ produciton in human leucocytes by monohydroxy fatty acids, *British J. Phamacology*, vol. 85, pp. 837–841 (1985).

Deleuran et al., "Cytokines in Rheumatoid Arthritis," *Scand. J. Rheumatol.*, vol. 25 (Suppl 104), pp. 1–38 (1996).

Denizot et al., "Effect of Cytokines and Lipid Mediators on the Synthesis of Interleukin 1β By Human Bone Marrow Stromal Cells," *Cytokine*, vol. 12(5), pp. 499–502 (2000).

Denizot et al., "Effects of Lipid Mediators on the Synthesis of Leukaemia Inhibitor Factor and Interleukin 6 by Human Bone Marrow Stromal Cells," *Cytokine*, vol. 10 (10), pp. 781–785 (1998).

Denizot et al., "Lipid Mediators Modulate the Synthesis of Interleukin 8 by Human–Bone Marrow Stromal Cells," *Cytokine*, vol. 11(8), pp. 606–610 (1999).

Ferrante et al., "Altered Responses of Human Macrophages to Lipopolysaccharide by Hydroperoxy Eicosatetraenoic Acid, Hydroxy Eicosatetraenoic Acid, and Arachidonic Acid," *J. Clinical Invest.*, vol. 99(6), pp. 1445–1452 (1997).

Fogh et al., 15–Hydoxy–Eicosatetraenoic Acid (15–HETE) Inhibits Carrageenan–Induced Experimental Arthritis and Reduces Synovial Fluid Leukotrike $B_4$ (LTB$_4$), *Prostaglandins*, vol. 37(2), pp. 213–228 (1989).

(List continued on next page.)

Primary Examiner—Kevin E. Weddington
(74) Attorney, Agent, or Firm—Patrick M. Ryan

(57) ABSTRACT

The topical use of HETE compounds to treat ophthalmic inflammatory disorders involving cytokines is disclosed.

5 Claims, No Drawings

OTHER PUBLICATIONS

Fogh et al., Improvement of psoriasis vulgaris after intralesional injections of 15–hydroxyeicosatetraenoic acid (15–HETE), *J. of the American Academy of Dermatology*, vol. 18(2), pp. 279–285 (1988).

Graeber et al., "15–Hydroxyeicosatetraenoic Acid Stimulates Migration Human Retinal Microvessel Endothelium In Vitro and Neovascularization In Vivo," *Prostaglandins*, vol. 39(6), pp. 665–673 (1990).

Hadjiagapiou et al., Metabolism of 15–Hydroxy–5,8,11, 13–eicosatetraenoic Acid by MOLT–4 Cells and Blood T–lymphocytes, *J. Biol. Chem.*, vol. 265(8), pp. 4369–4373 (1990).

Hamberg et al., "Identification of 15–hydroxy–5.8.11.13–eicosatetraenoic acid (15–HETE) as a major metabolite of arachidonic acid in human lung," Acta Physiol Scand., vol. 110; pp. 219–221 (1980).

Haviv et al., "Structural Requirements for the Inhibition of 5–Lipoxygenase by 15–Hydroxyeicosa–5,8,11,13–tetraenooc Acid Analogues," J. Med. Chem., vol. 30, pp. 254–263 (1987).

Heitmann et al., "Incorporation of 15–hydroxyeicosatrienoic acid in specific phospholipids of cultured human keratinocytes and psoriatic plaques," *Exp. Dermatol*, vol. 4, pp. 74–78 (1995).

Hutchinson, "Arachidonate 15–lipoxygenase; characteristics and potential biological significance," Eicosanoids, vol. 4, pp. 65–74 (1991).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kragbalie et al., "Intralesional Injection of 15(S)–Hydroxyeicosatetraenoic Acid in Psoriasis," *The Lancet*, p. 509 (Aug. 30, 1986).

Lai et al., "Effect of inhaled 15–(s)–hydroxyeicosatetraenoic acid on tracheobronchial clearance in normal human airways," *Thorax*, vol. 46, pp. 446–448 (1991).

Lai et al., "The effect of inhaled 15–(s)–hydroxyeicosatetraenoic acid (15–HETE) on airway calibre and non–specific responsiveness in normal and asthmatic human subjects," *Eur. Respir. J.*, vol. 3, pp. 38–45 (1990).

Legrand et al., "Substitution of 15–Hydroxyeicosatetraenoic Acid in the Phosphoinositide Signaling Pathway," J. of Biological Chemistry, vol. 266 (12), pp. 7570–7577 (1991).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," Journal of Clinical Investigation, vol. 72, pp. 122–127 (1983).

Martini et al., "Regiocontrol of Soybean Lipoxygenase Oxygenation. Application to the Chemoenzymatic Synthesis of Methyl 15(S)–HETE and Dimethyl 5(S)–, 15(S)–HETE," Journal of Organic Chemistry, vol. 61, pp. 9062–9064 (1996).

Masferrer et al., "12(R)–Hydroxyeicosatetraenoic Acid, An Endogenous corneal Arachidonate Metabolite, Lowers Intraocular Pressure in Rabbits," Investigative Ophthalmology and Visual Science, vol. 31(3); pp. 535–539 (1990).

Moore et al., "Murine Cerebral Microvascular Endothelium Incorporate and Metabolize 12–Hydroxyeicosatetraenoic Acid," *J. of Cellular Physiology*, vol. 137, pp. 75–85 (1988).

O'Flaherty et al., "5–Oxo–eicosanoids and Hernatopoietic Cytokines Cooperate in Stimulating Neutrophil Function and the Mitogen–activated Protein Kinase Pathway," *J. of Biological Chemistry*, vol. 271(30), pp. 17821–17828 (1996).

O'Flaherty, "5–Oxo–Eicosatetraenoate is a Broadly Active, Eosinophil–Selective Stimulus for Human Granulocytes," *The J. Of Immunology*, vol. 157, pp. 336–342 (1996).

Ohno, M.; Otsuka, M. Organic Reactions, vol. 37, Chpater I, pp. 1–55 (1989).

Pisarev et al., "Further Studies on the Antigoitrogenic Action of Iodoarachidonates," *Thyroidology*, vol. 4, pp. 27–29 (1992).

Pisarev et al., "Studies on the goiter inhibiting action of Iodolactones, "*European J. of Pharmacology*, vol. 258, pp. 33–37, (1994).

Profita et al., "Interleukin–4 Enhances 15–Lipoxygenase Activity and Incorporation of 15(S)–HETE into Cellular Phospholipids in Cultured Pulmonary Epithelial Cells," Am. J. Respir. Cell Mol. Biol., vol. 20, pp. 61–68 (1999).

Pupillo, "Role of Eicosanoids in T Cell Mitogenesis," Dissertation submitted at The George Washington University (1986).

Shelhamer et al., "The Effects of Arachinoids and Leukotrienes on the Release of Mucus from Human Airways," Chest Supplement, 24th Aspen Lung Conference, vol. 81(5); pp. 36S–37S (1982).

Simchowitz et al., "Carrier–mediated transport of lipoxin $A_4$ in human neutrophils," *American J. of Physiology*, vol. 267, pp. 1525–1534 (1994).

Smith et al., "Arachidonic Acid and 15(S)–Hydroxy–5,8, 11–Cis–13–Trans–Eicosatetraenoic Acid Modulate Human Polymorphonuclear Neutrophil Activiation by Monocyte Derived Neutrophil Activating Factor," *Biochemical and Biophysical Research Communications*, vol. 148(2), pp. 636–645 (1987).

Van Dijk et al., "15–Hydroxy–eicosatetraenoic Acid has Minor Anti–Inflammatory Properties in Colitis," *Agents and Actions*, vol. 38, pp. C120–121 (1993).

Wiggins et al., "12(S)–Hydroxy–5,8.10.14–Eicosatetraenoic Acid is a More Potent Neutrophil Chemoattractant Than the 12(R) Epimer in the Rat Cornea," Prostaglandins, vol. 49(2) pp. 131–141 (1990).

Xi et al., "Suppression of proto–oncogene (AP–1) in a model of skin epidermal hyperproliferation is reversed by topical application of 13–hydroxyoctadecadienoic acid and 15–hydroxyeicosatrienoic acid," *Prostaglandins, Leukotrienes and Essential Fatty Acids*, vol. 62(1), pp. 13–19 (2000).

Zhu et al., "Preview of Potential Therapeutic Applications of Leukotriene B4 inhibitors in Dermatology," *Skin Pharmacol Appl Skin Physiol*, vol. 13; pp. 235–245 (2000).

Ziboh, "Prostaglandins, Leukotrienes, and Hydroxy Fatty Acids in Epidermis," *Seminars in Dermatology*, vol. 11 (2), pp. 114–120 (1992).

Bhargava et al., "Ocular Allergic Disease," *Drugs of Today*, vol. 34 (11), pp. 957–971 (1998).

Limberg et al., "The effect of a new lipoxygenase inhibitor on the production of arachidonic acid metabolites during experimental herpes simplex keratitis," *Current Eye Research*, vol. 7(11), pp. 1131–1135 (1988).

Mastyugin et al., "Hypoxia–Induced Production of 12–Hydroxyeicosanoids in the Conreal Epithelium: Involvement of a Cytochome P–4504B1 Isoform," *J. of Pharmacology and Experimental Therapeutics*, vol. 289 (3); pp. 1611–1619 (1999).

\* cited by examiner

USE OF HYDROXYEICOSATETRAENOIC ACID COMPOUNDS TO TREAT OPHTHALMIC INFLAMMATORY DISORDERS

This application claims priority from U.S. Provisional Application, U.S. Ser. No. 60/389,115, filed Jun. 14, 2002.

The present invention is directed to the use of hydroxyeicosatetraenoic acid compounds to treat ophthalmic inflammation. In particular, the invention relates to the use of such analogs in patients that are not suffering from dry eye for the treatment and prevention of ophthalmic inflammatory disorders involving cytokine secretion.

BACKGROUND OF THE INVENTION

15-Hydroxyeicosatetraenoic acid ("15-HETE") is known to have inhibitory effects on leukotriene B4 production or its activity. See, for example, Zhu, et al., Skin Pharmacology and Applied Skin Physiology, 13(5):235–45 (September–October 2000); and Heitmann, et al., Experimental Dermatology, 4(2):74–8 (April 1995). 15-HETE is also reported to have minor anti-inflammatory properties in colitis. See Van Dijk, et al., Agents and Actions, 38 Spec. No. C120-1 (1993).

U.S. Pat. No. 5,696,166 (Yanni et al.) discloses compositions containing hydroxyeicosatetraenoic acid ("HETE") derivatives and methods of using them topically for treating dry eye. Yanni et al. discovered that compositions comprising HETE derivatives increase ocular mucin secretion and are thus useful in treating dry eye.

Other than the use of 15-HETE and certain analogs for treating dry eye, HETE compounds have not been reported to be useful in treating inflammatory conditions of the eye, particularly in treating conditions involving the production of pro-inflammatory cytokines. Reports of the effects of 15-HETE and analogs of 15-HETE on cytokine inhibition in other tissues are varied. See, for example, Denizot, et al., Cytokine, 11(8):606–10 (August 1999) (" . . . 15-HETE (1 µM to 0.1 nM) [has] no effect on the spontaneous and serum-induced production of IL-8 by human bone marrow stromal cells"); Denizot, et al., Cytokine, 10(10):781–5 (October 1998) (" . . . 15-HETE . . . [has] no effect on the spontaneous, serum- and cytokine-induced IL-6 synthesis by bone marrow stromal cells; and WO 96/11908, which discloses that certain modified polyunsaturated fatty acids have the ability to suppress cytokine production and cytokine action and are useful as anti-malarial, anti-infective or anti-inflammatory agents. WO 96/11908 does not mention any ophthalmic inflammatory disorders.

SUMMARY OF THE INVENTION

The present invention is directed to methods of using HETE compounds to treat or prevent ophthalmic inflammatory conditions in patients that are not suffering from dry eye. In particular, the present invention is directed toward the topical ophthalmic use of HETE compounds to treat or prevent ophthalmic inflammatory conditions involving cytokines. Such ophthalmic inflammatory conditions include, but are not limited to, conjunctivitis; iritis; uveitis; episcleritis; scleritis; keratitis; endophthalmitis; and blepharitis.

DETAILED DESCRIPTION OF THE INVENTION

As used herein, "HETE compound" or "HETE compounds" means a compound of formulas I–XI.
I–III:

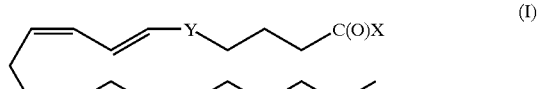
(I)

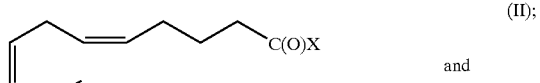
(II);
and

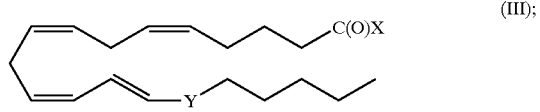
(III);

wherein:
X is $O^-M^+$, OR or NHR';
$M^+$ is $Na^+$, $K^+$, $Li^+$, $Cs^+$, and $(A)_4N^+$; and A is independently H, alkyl, cycloalkyl, (cycloalkyl)alkyl, alkyl (cycloalkyl), aryl, arylalkyl, heteroaryl, or $(A)_4N^+$ forms a heteroaryl, heterocycloalkenyl or heterocycloalkyl ring;
R is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;
R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and
Y is

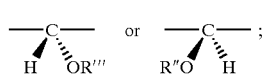

wherein R" is H or C(O)R;

IV:

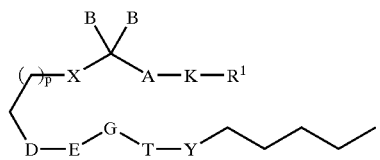

wherein:
$R^1$ is $CO_2R$, $CONR^2R^3$, $CH_2OR^4$, $CH_2NR^5R^6$, $CH_2N_3$, $CH_2$—Hal, $CH_2NO_2$, $CH_2SR^{20}$, $COSR^{21}$, or 2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;

OR$^4$ comprises a free or functionally modified hydroxy group, e.g., R$^4$ is H, acyl; alkyl, cycloalkyl, aralkyl, or aryl;

Hal is F, Cl, Br or I;

SR$^{20}$ comprises a free or functionally modified thiol group;

R$^{21}$ is H, or COSR$^{21}$ forms a pharmaceutically acceptable salt or a pharmaceutically acceptable thioester;

K is C$_2$–C$_8$ alkyl, alkenyl, or alkynyl, or a C$_3$–C$_8$ allenyl group;

A and X are the same or different and are a direct bond, CH$_2$, NR$^7$, O, or S, with the proviso that at least one of A and X is NR$^7$, O, or S;

B is H, or BB together comprises a double bonded O, S, or NR$^8$, with the proviso that BB comprises a double bonded O, S, or NR$^8$ when A and X are the same or different and are NR$^7$, O, or S; wherein:

NR$^7$ and NR$^8$ are the same or different and comprise a functionally modified amino group, e.g., R$^7$ and R$^8$ are the same or different and are H, alkyl, cycloalkyl, aryl, aralkyl, acyl, OH, or alkoxy;

p is 0 or 1;

D-E, G-H are the same or different and are CH$_2$CH$_2$, CH=CH, or C≡C; and

Y is C(O) (i.e. a carbonyl group) or Y is

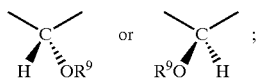

wherein R$^9$O constitutes a free or functionally modified hydroxy group;

V:

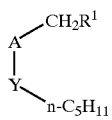

wherein:

R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$, or 2,3,4,5-tetrazol-1-yl, where:

R is H or a pharmaceutically acceptable cation, or CO$_2$R forms a pharmaceutically acceptable ester moiety;

NR$^2$R$^3$, NR$^5$R$^6$ are the same or different and comprise a free or functionally modified amino group;

OR$^4$ comprises a free or functionally modified hydroxy group;

Hal is F, Cl, Br, or I;

R$^{20}$ is H, alkyl, acyl;

R$^{21}$ is H or a pharmaceutically acceptable cation, or COSR$^{21}$ forms a pharmaceutically acceptable thioester moiety;

A is L$_1$-A$_1$-L$_2$, L$_1$-A$_2$-L$_2$, L$_3$-A$_2$-L$_4$, or L$_5$-A$_2$—L$_3$;

A$_1$ is CH$_2$CH$_2$;

A$_2$ is

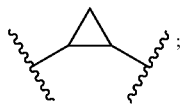

L$_1$ is CH$_2$-B-D;

B and D are the same or different and are CH$_2$CH$_2$, CH=CH, or C≡C;

L$_2$ is CH$_2$-K-CH$_2$CH$_2$;

K is CH$_2$CH$_2$, CH=CH, or C≡C;

L$_3$ is CH$_2$CH$_2$CH$_2$, CH$_2$CH=CH, CH$_2$C≡C, CH=CHCH$_2$, C≡CCH$_2$, or CH=C=CH;

L$_4$ is X—CH$_2$CH$_2$;

X is CH$_2$CH$_2$CH=CH, CH$_2$CH$_2$C≡C, CH$_2$CH$_2$CH$_2$CH$_2$, CH$_2$CH=CHCH$_2$, CH$_2$C≡CCH$_2$, CH=CHCH$_2$CH$_2$, C≡CCH$_2$CH$_2$, CH$_2$CH=C=CH, or CH=C=CHCH$_2$;

L$_5$ is CH$_2$CH$_2$-B-D; and

Y is C(O) (i.e. a carbonyl group) or Y is

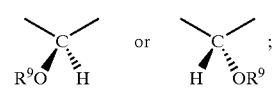

wherein R$^9$O constitutes a free or functionally modified hydroxy group;

VI:

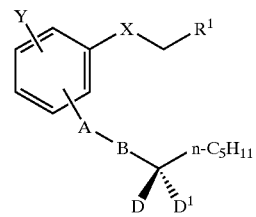

wherein:

R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$ or 2,3,4,5-tetrazol-1-yl, wherein:

R is H or CO$_2$R forms a pharmaceutically acceptable salt or a pharmaceutically acceptable ester;

NR$^2$R$^3$ and NR$^5$R$^6$ are the same or different and comprise a free or functionally modified amino group, e.g., R$^2$, R$^3$, R$^5$ and R$^6$ are the same or different and are H, alkyl, cycloalkyl, aralkyl, aryl, OH or alkoxy, with the proviso that at most only one of R$^2$ and R$^3$ are OH or alkoxy and at most only one of R$^5$ and R$^6$ are OH or alkoxy;

OR$^4$ comprises a free or functionally modified hydroxy group, e.g., R$^4$ is H, acyl; alkyl, cycloalkyl, aralkyl or aryl;

Hal is F, Cl, Br or I;

SR$^{20}$ comprises a free or functionally modified thiol group;

R$^{21}$ is H or COSR$^{21}$ forms a pharmaceutically acceptable salt or a pharmaceutically acceptable thioester;

X is C$_2$–C$_5$ alkyl, alkynyl, or alkenyl or a C$_3$–C$_5$ allenyl group;

Y is H, free or functionally modified hydroxy group, halo, trihalomethyl, free or functionally modified amino group, free or functionally modified thiol group, C(O)R$^7$, or alkyl;

R$^7$ is H, OH, alkyl, alkoxy, amino, alkylamino or alkoxyamino;

A is a direct bond or C$_{1-3}$ alkyl;

B is $CH_2CH_2$, cis- or trans-$CH=CH$, or $C\equiv C$; and
one of D and $D^1$ is H and the other is a free or functionally modified OH group, or $DD^1$ together comprises a double bonded oxygen;

VII:

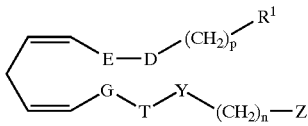

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
  R is H or $CO_2R$ forms a pharmaceutically acceptable salt or a pharmaceutically acceptable ester;
  $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
  $OR^4$ comprises a free or functionally modified hydroxy group, e.g., $R^4$ is H, acyl; alkyl, cycloalkyl, aralkyl or aryl;
  Hal is F, Cl, Br or I;
  $SR^{20}$ comprises a free or functionally modified thiol group;
  $R^{21}$ is H or $COSR^{21}$ forms a pharmaceutically acceptable salt or a pharmaceutically acceptable thioester;
E—D is $CH_2CH_2CH_2$ or cis-$CH_2CH=CH$; or E is trans-$CH=CH$ and D is $CH(OH)$ in either configuration, wherein the OH is free or functionally modified; or E is $CH_2CH_2$ and D is a direct bond;
p is 1 or 3 when E-D is $CH_2CH_2CH_2$ or cis-$CH_2CH=CH$, or when E is trans-$CH=CH$ and D is $CH(OH)$ in either configuration, wherein the OH is free or functionally modified; or p is 0 when E is $CH_2CH_2$ and D is a direct bond;
G-T is $CH_2CH_2$, $CH(SR^7)CH_2$ or trans-$CH=CH$;
$R^7$ is H, alkyl, aryl, aralkyl, cycloalkyl or acyl;
Y is CH(OH) in either configuration, in which the OH is free of functionally modified, or $C=O$ (i.e., a carbonyl group);
n is 0, 2 or 4; and
Z is $CH_3$, $CO_2R$, $CONR^2R^3$ or $CH_2OR^4$;

VIII:

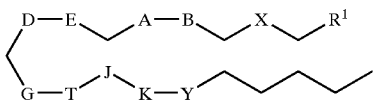

wherein:
$R^1$ is $(CH_2)_nCO_2R$, $(CH_2)_nCONR^2R^3$, $(CH_2)_nCH_2OR^4$, $(CH_2)_nCH_2NR^5R^6$, $(CH_2)_nCH_2N_3$, $(CH_2)_nCH_2Hal$, $(CH_2)_nCH_2NO_2$, $(CH_2)_nCH_2SR^{20}$, $(CH_2)_nCOSR^{21}$ or $(CH_2)_n$-2,3,4,5-tetrazol-1-yl, wherein:
  R is H or $CO_2R$ forms a pharmaceutically acceptable salt or a pharmaceutically acceptable ester;
  $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
  $OR^4$ comprises a free or functionally modified hydroxy group, e.g., $R^4$ is H, acyl; alkyl, cycloalkyl, aralkyl, or aryl;
  Hal is F, Cl, Br or I;
  $SR^{20}$ comprises a free or functionally modified thiol group;
  $R^{21}$ is H or $COSR^{21}$ forms a pharmaceutically acceptable salt or a pharmaceutically acceptable thioester;
  n is 0 or 2;
X is O, $S(O)_p$, $NR^7$ or $CH_2$, with the proviso that X cannot be $CH_2$ when n is 0;
p is 0, 1 or 2;
$NR^7$ comprises a free or functionally modified amino group, e.g., $R^7$ is H, alkyl, cycloalkyl, aralkyl, aryl, OH or alkoxy,
A-B, D-E, G-T and J-K are the same or different and are $CH_2CH_2$, $CH=CH$ or $C\equiv C$, with the proviso that at least one of A-B, D-E, G-T and J-K must be $CH=CH$ or $C\equiv C$; and
Y is C(O) (i.e., a carbonyl), or Y is

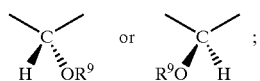

wherein $R^9O$ constitutes a free or functionally modified hydroxy group;

IX:

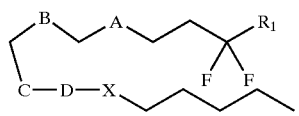

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
  R is H or $CO_2R$ forms a pharmaceutically acceptable salt or a pharmaceutically acceptable ester;
  $NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
  $OR^4$ comprises a free or functionally modified hydroxy group, e.g., $R^4$ is H, acyl; alkyl, cycloalkyl, aralkyl, or aryl;
  Hal is F, Cl, Br or I;
  $SR^{20}$ comprises a free or functionally modified thiol group;
  $R^{21}$ is H or $COSR^{21}$ forms a pharmaceutically acceptable salt or a pharmaceutically acceptable thioester;
A, B, C and D are the same or different and are $C_1$–$C_5$ alkyl, alkenyl, or alkynyl or a $C_3$–$C_5$ allenyl group;
X is C(O) (i.e. a carbonyl group) or X is

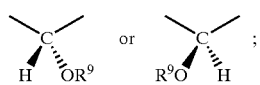

wherein $R^9O$ constitutes a free or functionally modified hydroxy group;

X:

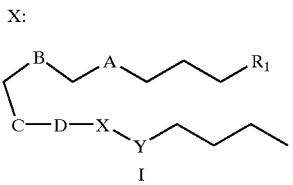

wherein:
$R^1$ is $(CH_2)_nCO_2R$, $(CH_2)_nCONR^2R^3$, $(CH_2)_nCH_2OR^4$, $(CH_2)_nCH_2NR^5R^6$, $(CH_2)_nCH_2N_3$, $(CH_2)_nCH_2Hal$, $(CH_2)_nCH_2NO_2$, $(CH_2)_nCH_2SR^{20}$, $(CH_2)_nCOSR^{21}$ or $(CH_2)_n$-2,3,4,5-tetrazol-1-yl, wherein:

R is H or $CO_2R$ forms a pharmaceutically acceptable salt or a pharmaceutically acceptable ester;

$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;

$OR^4$ comprises a free or functionally modified hydroxy group, e.g., $R^4$ is H, acyl; alkyl, cycloalkyl, aralkyl, or aryl; Hal is F, Cl, Br or I;

$SR^{20}$ comprises a free or functionally modified thiol group; $R^{21}$ is H or $COSR^{21}$ forms a pharmaceutically acceptable salt or a pharmaceutically acceptable thioester;

n is 0 or 2;

A, B, C and D is $C_1$–$C_5$ alkyl, alkenyl, or alkynyl or a $C_3$–$C_5$ allenyl group;

Y is

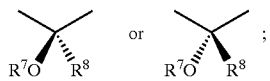

wherein $R^8$ is H or $CH_3$, and
X is $CH_2$, $CH(CH_3)$ or $C(CH_3)_2$; or
Y is $CH_2$, $CH(CH_3)$ or $C(CH_3)_2$, and X is

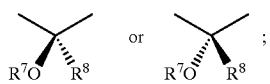

wherein $R^8$ is H or $CH_3$, with the proviso that Y cannot be $CH_2$ when X is

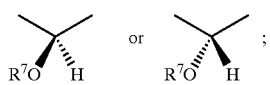

and
$R^7O$ comprises a free or functionally modified hydroxy group; and

XI:

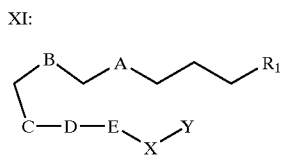

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H or a pharmaceutically acceptable cation, or $CO_2R$ forms a pharmaceutically acceptable ester moiety;

$NR^2R^3$, $NR^5R^6$ are the same or different and comprise a free or functionally modified amino group;

$OR^4$ comprises a free or functionally modified hydroxy group;

Hal is F, Cl, Br, or I;

$SR^{20}$ comprises a free or functionally modified thiol group;

$R^{21}$ is H or a pharmaceutically acceptable cation, or $COSR^{21}$ forms a pharmaceutically acceptable thioester moiety;

A, B, C, D are the same or different and are $C_1$–$C_5$ alkyl, $C_2$–$C_5$ alkenyl, $C_{1-5}$ cyclopropyl, $C_2$–$C_5$ alkynyl, or a $C_3$–$C_5$ allenyl group;

E is

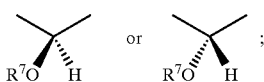

where $OR^7$ comprises a free or functionally modified hydroxy group;

$X=(CH_2)_m$ or $(CH_2)_mO$, where m=1–6; and

Y=a phenyl ring optionally substituted with alkyl, halo, trihalomethyl, acyl, or a free or functionally modified hydroxy, amino, or thiol group; or $X-Y=(CH_2)_pY^1$; where p=0–6; and

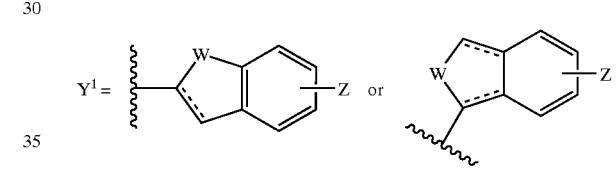

wherein:
$W=CH_2$, O, $S(O)_q$, $NR^8$, $CH_2CH_2$, $CH=CH$, $CH_2O$, $CH_2S(O)_q$, $CH=N$, or $CH_2NR^8$; where q=0–2, and $R^8$=H, alkyl, or acyl;

Z=H, alkyl, acyl, halo, trihalomethyl, or a free or functionally modified amino, thiol, or hydroxy group; and ————=single or double bond;

or X—Y=cyclohexyl.

Preferred HETE compounds include the compounds of formulas I–III wherein X is a pharmaceutically acceptable salt containing a cation selected from the group consisting of: $Na^+$; $K^+$; $Li^+$; $Cs^+$; and $(A)_4N^+$; and A is independently H, alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring.

Included within the scope of the present invention are the individual enantiomers of the HETE compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis*; J. D. Morrison and J. W. Scott, Eds.; Academic Press Publishers: New York, 1983–1985, volumes 1–5; *Principles of Asymmetric Synthesis*; R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by*

*HPLC*; G. Subramanian, Ed.; VCH Publishers: New York, 1994; *Chiral Separations by HPLC*; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

The term "free thiol group" means an SH. The term "functionally modified thiol group" means an SH which has been functionalized to form: a thioether, where an alkyl, aryl, cycloalkyl, heterocycloalkyl, alkenyl, cycloalkenyl, heterocycloalkenyl, alkynyl, or heteroaryl group is substituted for the hydrogen; or a thioester, in which an acyl group is substituted for the hydrogen. Preferred moieties include SH, $SC(O)CH_3$, $SCH_3$, $SC_2H_5$, $SCH_2C(O)C_2H_5$, and $SCH_2C(O)CH_3$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "$C_1$–$C_5$ cyclopropyl" means an alkyl chain of 1 to 5 carbon atoms containing a cyclopropyl group wherein the cyclopropyl group may start, be contained in or terminate the alkyl chain.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon-carbon double bond, the chain being optionally interrupted by one or more heteroatoms. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon-carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group, respectively, bonded from its oxygen atom to the carbon of a carbonyl group, the carbonyl group itself being bonded to another atom through its carbon atom.

According to the methods of the present invention a HETE compound of formulas I–XI is applied topically to the eye. The compositions used in the methods of the present invention comprise a pharmaceutically effective amount of one or more HETE compounds of formulas I–XI and a pharmaceutically acceptable carrier. Suitable pharmaceutical carriers are known in the art and include, but are not limited to, ophthalmically acceptable solutions, suspensions and other dosage forms for topical administration. Aqueous solutions are generally preferred, based on ease of formulation, biological compatibility, as well as a patient's ability to easily administer such compositions by means of instilling one to two drops of the solutions in the affected eyes. However, the compositions may also be suspensions, viscous or semi-viscous gels, or other types of solid or semi-solid compositions. Suspensions may be preferred for compounds of formulas I–XI which are less soluble in water.

As used herein, the term "pharmaceutically effective amount" refers to an amount of one or more compounds of formulas I–XI that, when administered to a patient, reduces, eliminates or prevents ophthalmic inflammation. Generally, the compounds of formulas I–XI will be contained in a composition of the present invention in a concentration range of about 0.000001 to 10 percent weight/volume ("% w/v"). Preferably, the compositions will contain one or more compounds of formulas I–XI in a concentration of from about 0.00001–0.01% w/v.

Various tonicity agents may be included in the compositions of the present invention to adjust tonicity, preferably to that of natural tears for ophthalmic compositions. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added. In general, however, the compositions will have one or more tonicity agents in a total concentration sufficient to cause the composition to have an osmolality of about 200–400 mOsm.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. In general, however, the buffering agent will be present in an amount sufficient to hold the pH within the range 6.5–8.0, preferably 6.8–7.6.

Antioxidants may be added to compositions of the present invention to protect the compounds of formulas I–XI from oxidation during storage and/or or to provide antioxidant effects in the eye. Examples of such antioxidants include, but are not limited to, vitamin E and analogs thereof, ascorbic acid and derivatives, and butylated hydroxyanisole (BHA).

The compositions of the present invention may be used to treat or prevent ophthalmic inflammatory conditions involving cytokine secretion. Such conditions include, but are not limited to, non-infectious keratoconjunctivitis (including, but not limited to, seasonal allergic conjunctivitis, atopic keratoconjunctivitis, vernal keratoconjunctivitis, contact dermatoconjunctivitis, giant papillary conjunctivitis, contact lens-induced keratoconjunctivitis, superior limbic keratoconjunctivitis, toxic conjunctivitis, ocular cicatricial pemphigoid, and Thygeson's superficial punctate keratopathy), uveitis, episcleritis, scleritis, iritis, blepharitis, keratitis, endophthalmitis, canaliculitis, dacryocystitis, preseptal cellulitis, orbital cellulitis. seborrheic blepharitis, meibomian gland dysfunction, acne rosacea, filamentary keratopathy, neurotrophic keratopathy, corneal erosions, corneal dystrophies, iridocorneal endothelial syndrome, noninfectious ulcerative keratitis. Such inflammatory conditions involving cytokine secretion also include inflammation due to ocular trauma, including, but not limited to inflammation due to corneal abrasions, corneal foreign body, corneal laceration and chemical burn, and iatrogenic inflammatory conditions related to post-LASIK, post-LASEK, post-PRK, post-cataract surgery, post-glaucoma filtration surgery. Such inflammatory conditions involving cytokine secretion also include inflammation due to degeneration and corneal ectactic disorders, including, but not limited to, ptyrygium, pinguecula, band-shaped keratopathy, Salzmann's nodular degeneration, keratoconus, and Terrien's marginal degeneration. Such inflammatory conditions involving cytokine secretion also include, but are not limited to, entropion, ectropion, trichiasis, lagophthalmos and floppy eyelid syndrome.

The compositions of the present invention also may be used alone or in combination with antimicrobial or antiviral agents in diseases primarily infectious in nature but involving an inflammatory component, including, but not limited to infectious conjunctivitis and infectious keratitis conditions, such as bacterial conjunctivitis, viral conjunctivitis, chlamydial conjunctivitis, fungal conjunctivitis, bacterial keratitis, fungal keratitis and acanthamoeba keratitis, herpetic diseases of the eye, infectious endophthalmitis, and staphyloccocal blepharitis.

Preferably, the compositions of the present invention are used to treat ophthalmic inflammatory conditions selected from the group consisting of conjunctivitis (non-infectious keratoconjunctivitis and infectious conjunctivitis); iritis; uveitis; episcleritis; scleritis; keratitis; endophthalmitis; blepharitis; and iatrogenic inflammatory conditions.

The following examples are presented to illustrate various aspects of the present invention, but are not intended to limit the scope of the invention in any respect.

EXAMPLE 1

| Ingredient | Amount (% w/v) |
|---|---|
| Compound of formulas I–XI | 0.00001–0.01 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method. The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of the compound of formulas I–XI as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient. Preferably, the above process is performed using glass, plastic or other non-metallic containers or containers lined with such materials.

EXAMPLE 2

| Ingredient | Amount (% w/v) |
|---|---|
| Compound of formulas I–XI | 0.00001–0.01 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 6.5–8 |
| Purified Water | q.s. 100% |

The above formulation may be made by a method similar to the method described in Example 1.

EXAMPLE 3

| Ingredient | Amount (% w/v) |
|---|---|
| Compound of formulas I–XI | 0.00001–0.01 |
| Polyoxyl 40 Stearate | 0.1 |
| Ethanol | 0.005–0.2 |
| Boric Acid | 0.25 |
| Sodium Chloride | 0.75 |
| NaOH/HCl | q.s., pH = 6.5–8 |
| Purified Water | q.s. 100% |

The above formulation may be made by a method similar to the method described in Example 1.

EXAMPLE 4

The following is an example of a composition of the present invention using an artificial tears carrier:

| Ingredient | Amount (% w/v) |
|---|---|
| Compound of formulas I–XI | 0.00001–0.01 |
| HPMC | 0.3 |
| Dextran 70 | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

The above formulation may be made by a method similar to the method described in Example 1.

EXAMPLE 5

Primary human corneal fibroblast cells were obtained from one donor and grown to confluence in Ham's F-10 medium. Fibroblasts were transferred to serum-free media and were pretreated for 30 minutes with various concentrations of 15(S)-HETE. The cells were then stimulated with 10 ng/ml IL-1β for 3 hours and aliquots of the supernatants were assayed for IL-6 by ELISA. Data were normalized by the amount of double stranded DNA (dsDNA) extracted from the cells. The results are shown below in Table 1.

TABLE 1

| Concentration of 15(S)-HETE ($\mu$g) | % Inhibition of IL-6 (pg/$\mu$g dsDNA) |
|---|---|
| 0.5 | 53.1 |
| 1 | 67.9* |
| 2 | 88.6** |
| 3 | 90.4** |

*$p < 0.05$,
**$p < 0.01$
Two-tail Dunnett's t-test compared to IL-1β stimulated cells The results shown in Table 1 demonstrate that 15-HETE dose-dependently inhibited IL-6 release from primary human corneal fibroblast cells. The $IC_{50}$ for IL-6 inhibition was less than 0.5 $\mu$M.

The invention in its broader aspects is not limited to the specific details shown and described above. Departures may be made from such details within the scope of the accompanying claims without departing from the principles of the invention and without sacrificing its advantages.

What is claimed is:

1. A method of treating ophthalmic inflammatory disorders in a patient that is not suffering from dry eye, wherein the ophthalmic inflammatory disorder is selected from the group consisting of conjunctivitis; iritis; uveitis; episcleritis; scleritis; keratitis; endophthalmitis; blepharitis; and iatrogenic inflammatory conditions, and wherein the method comprises topically administering to the patient a composition comprising a HETE compound of formulas I–XI:

I–III:

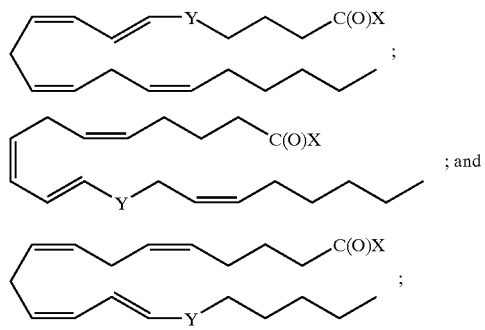

wherein:
X is $O^-M^+$, OR or NHR';

$M^+$ is $Na^+$, $K^+$, $Li^+$, $Cs^+$, and $(A)_4N^+$; and A is independently H, alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring;

R is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;

R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and Y is

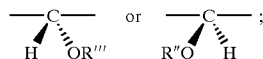

wherein R" is H or C(O)R;

IV:

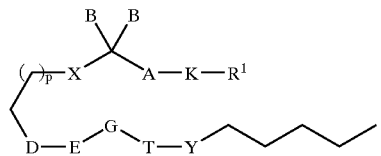

wherein:
$R^1$ is $CO_2R$, $CONR^2R^3$, $CH_2OR^4$, $CH_2NR^5R^6$, $CH_2N_3$, $CH_2$—Hal, $CH_2NO_2$, $CH_2SR^{20}$, $COSR^{21}$, or 2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;

$OR^4$ comprises a free or functionally modified hydroxy group, e.g., $R^4$ is H, acyl; alkyl, cycloalkyl, aralkyl, or aryl;

Hal is F, Cl, Br or I;

$SR^{20}$ comprises a free or functionally modified thiol group;

$R^{21}$ is H, or $COSR^{21}$ forms a pharmaceutically acceptable salt or a pharmaceutically acceptable thioester;

K is $C_2$–$C_8$ alkyl, alkenyl, or alkynyl, or a $C_3$–$C_8$ allenyl group;

A and X are the same or different and are a direct bond, $CH_2$, $NR^7$, O, or S, with the proviso that at least one of A and X is $NR^7$, O, or S;

B is H, or BB together comprises a double bonded O, S, or $NR^8$, with the proviso that BB comprises a double bonded O, S, or $NR^8$ when A and X are the same or different and are $NR^7$, O, or S; wherein:

$NR^7$ and $NR^8$ are the same or different and comprise a functionally modified amino group, e.g., $R^7$ and $R^8$ are the same or different and are H, alkyl, cycloalkyl, aryl, aralkyl, acyl, OH, or alkoxy;

p is 0 or 1;

D-E, G-H are the same or different and are $CH_2CH_2$, CH=CH, or C≡C; and

Y is C(O) (i.e. a carbonyl group) or Y is

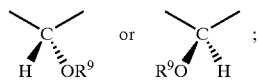

wherein $R^9O$ constitutes a free or functionally modified hydroxy group;

V:

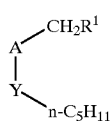

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H or a pharmaceutically acceptable cation, or $CO_2R$ forms a pharmaceutically acceptable ester moiety;

$NR^2R^3$, $NR^5R^6$ are the same or different and comprise a free or functionally modified amino group;

$OR^4$ comprises a free or functionally modified hydroxy group;

Hal is F, Cl, Br, or I;

$R^{20}$ is H, alkyl, acyl;

$R^{21}$ is H or a pharmaceutically acceptable cation, or $COSR^{21}$ forms a pharmaceutically acceptable thioester moiety;

A is $L_1$-$A_1$-$L_2$, $L_1$-$A_2$-$L_2$, $L_3$-$A_2$-$L_4$, or $L_5$-$A_2$—$L_3$;
$A_1$ is $CH_2CH_2$;
$A_2$ is

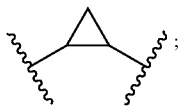

$L_1$ is $CH_2$-B-D;
B and D are the same or different and are $CH_2CH_2$, $CH=CH$, or $C\equiv C$;
$L_2$ is $CH_2$-K-$CH_2CH_2$;
K is $CH_2CH_2$, $CH=CH$, or $C\equiv C$;
$L_3$ is $CH_2CH_2CH_2$, $CH_2CH=CH$, $CH_2C\equiv C$, $CH=CHCH_2$, $C\equiv CCH_2$, or $CH=C=CH$;
$L_4$ is X—$CH_2CH_2$;
X is $CH_2CH_2CH=CH$, $CH_2CH_2C\equiv C$, $CH_2CH_2CH_2CH_2$, $CH_2CH=CHCH_2$, $CH_2C\equiv CCH_2$, $CH=CHCH_2CH_2$, $C\equiv CCH_2CH_2$, $CH_2CH=C=CH$, or $CH=C=CHCH_2$;
$L_5$ is $CH_2CH_2$-B-D; and
Y is C(O) (i.e. a carbonyl group) or Y is

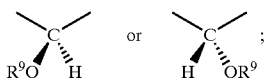

wherein $R^9O$ constitutes a free or functionally modified hydroxy group;

VI:

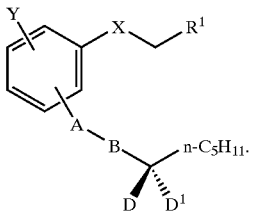

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH or alkoxy, with the proviso that at most only one of $R^2$ and $R^3$ are OH or alkoxy and at most only one of $R^5$ and $R^6$ are OH or alkoxy;
$OR^4$ comprises a free or functionally modified hydroxy group, e.g., $R^4$ is H, acyl; alkyl, cycloalkyl, aralkyl or aryl;
Hal is F, Cl, Br or I;
$SR^{20}$ comprises a free or functionally modified thiol group;
$R^{21}$ is H or $COSR^{21}$ forms a pharmaceutically acceptable salt or a pharmaceutically acceptable thioester;
X is $C_2$–$C_5$ alkyl, alkynyl, or alkenyl or a $C_3$–$C_5$ allenyl group;
Y is H, free or functionally modified hydroxy group, halo, trihalomethyl, free or functionally modified amino group, free or functionally modified thiol group, $C(O)R^7$, or alkyl;

$R^7$ is H, OH, alkyl, alkoxy, amino, alkylamino or alkoxyamino;
A is a direct bond or $C_{1-3}$ alkyl;
B is $CH_2CH_2$, cis- or trans-$CH=CH$, or $C\equiv C$; and
one of D and $D^1$ is H and the other is a free or functionally modified OH group, or $DD^1$ together comprises a double bonded oxygen;

VII:

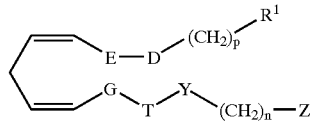

wherein:
$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:
R is H or $CO_2R$ forms a pharmaceutically acceptable salt or a pharmaceutically acceptable ester;
$NR^2R^3$ and $NR^5R^6$ are the same or different and comprise a free or functionally modified amino group, e.g., $R^2$, $R^3$, $R^5$ and $R^6$ are the same or different and are H, alkyl, cycloalkyl, aralkyl, aryl, OH, or alkoxy, with the proviso that at most only one of $R^2$ and $R^3$ are OH or alkoxy and at most only one of $R^5$ and $R^6$ are OH or alkoxy;
$OR^4$ comprises a free or functionally modified hydroxy group, e.g., $R^4$ is H, acyl; alkyl, cycloalkyl, aralkyl or aryl;
Hal is F, Cl, Br or I;
$SR^{20}$ comprises a free or functionally modified thiol group;
$R^{21}$ is H or $COSR^{21}$ forms a pharmaceutically acceptable salt or a pharmaceutically acceptable thioester;
E–D is $CH_2CH_2CH_2$ or cis-$CH_2CH=CH$; or E is trans-$CH=CH$ and D is CH(OH) in either configuration, wherein the OH is free or functionally modified; or E is $CH_2CH_2$ and D is a direct bond;
p is 1 or 3 when E–D is $CH_2CH_2CH_2$ or cis-$CH_2CH=CH$, or when E is trans-$CH=CH$ and D is CH(OH) in either configuration, wherein the OH is free or functionally modified; or p is 0 when E is $CH_2CH_2$ and D is a direct bond;
G-T is $CH_2CH_2$, $CH(SR^7)CH_2$ or trans-$CH=CH$;
$R^7$ is H, alkyl, aryl, aralkyl, cycloalkyl or acyl;
Y is CH(OH) in either configuration, in which the OH is free of functionally modified, or $C=O$ (i.e., a carbonyl group);
n is 0, 2 or 4; and
Z is $CH_3$, $CO_2R$, $CONR^2R^3$ or $CH_2OR^4$;

VIII:

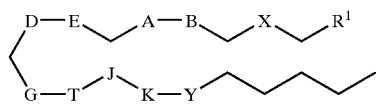

wherein:
$R^1$ is $(CH_2)_nCO_2R$, $(CH_2)_nCONR^2R^3$, $(CH_2)_nCH_2OR^4$, $(CH_2)_nCH_2NR^5R^6$, $(CH_2)_nCH_2N_3$, $(CH_2)_nCH_2Hal$, $(CH_2)_nCH_2NO_2$, $(CH_2)_nCH_2SR^{20}$, $(CH_2)_nCOSR^{21}$ or $(CH_2)_n$-2,3,4,5-tetrazol-1-yl, wherein:

R is H or CO$_2$R forms a pharmaceutically acceptable salt or a pharmaceutically acceptable ester;

NR$^2$R$^3$ and NR$^5$R$^6$ are the same or different and comprise a free or functionally modified amino group, e.g., R$^2$, R$^3$, R$^5$ and R$^6$ are the same or different and are H, alkyl, cycloalkyl, aralkyl, aryl, OH, or alkoxy, with the proviso that at most only one of R$^2$ and R$^3$ are OH or alkoxy and at most only one of R$^5$ and R$^6$ are OH or alkoxy;

OR$^4$ comprises a free or functionally modified hydroxy group, e.g., R$^4$ is H, acyl; alkyl, cycloalkyl, aralkyl, or aryl;

Hal is F, Cl, Br or I;

SR$^{20}$ comprises a free or functionally modified thiol group;

R$^{21}$ is H or COSR$^{21}$ forms a pharmaceutically acceptable salt or a pharmaceutically acceptable thioester;

n is 0 or 2;

X is O, S(O)$_p$, NR$^7$ or CH$_2$, with the proviso that X cannot be CH$_2$ when n is 0;

p is 0, 1 or 2;

NR$^7$ comprises a free or functionally modified amino group, e.g., R$^7$ is H, alkyl, cycloalkyl, aralkyl, aryl, OH or alkoxy, A-B, D-E, G-T and J-K are the same or different and are CH$_2$CH$_2$, CH=CH or C≡C, with the proviso that at least one of A-B, D-E, G-T and J-K must be CH=CH or C≡C; and Y is C(O) (i.e., a carbonyl), or Y is

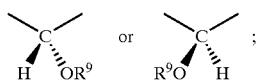

wherein R$^9$O constitutes a free or functionally modified hydroxy group;

IX:

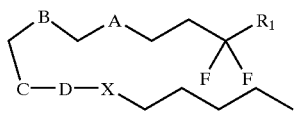

wherein:

R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$ or 2,3,4,5-tetrazol-1-yl, wherein:

R is H or CO$_2$R forms a pharmaceutically acceptable salt or a pharmaceutically acceptable ester;

NR$^2$R$^3$ and NR$^5$R$^6$ are the same or different and comprise a free or functionally modified amino group, e.g., R$^2$, R$^3$, R$^5$ and R$^6$ are the same or different and are H, alkyl, cycloalkyl, aralkyl, aryl, OH, or alkoxy, with the proviso that at most only one of R$^2$ and R$^3$ are OH or alkoxy and at most only one of R$^5$ and R$^6$ are OH or alkoxy;

OR$^4$ comprises a free or functionally modified hydroxy group, e.g., R$^4$ is H, acyl; alkyl, cycloalkyl, aralkyl, or aryl;

Hal is F, Cl, Br or I;

SR$^{20}$ comprises a free or functionally modified thiol group;

R$^{21}$ is H or COSR$^{21}$ forms a pharmaceutically acceptable salt or a pharmaceutically acceptable thioester;

A, B, C and D are the same or different and are C$_1$–C$_5$ alkyl, alkenyl, or alkynyl or a C$_3$–C$_5$ allenyl group;

X is C(O) (i.e. a carbonyl group) or X is

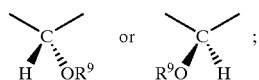

wherein R$^9$O constitutes a free or functionally modified hydroxy group;

X:

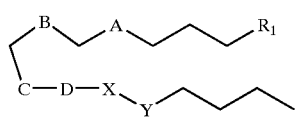

wherein:

R$^1$ is (CH$_2$)$_n$CO$_2$R, (CH$_2$)$_n$CONR$^2$R$^3$, (CH$_2$)$_n$CH$_2$OR$^4$, (CH$_2$)$_n$CH$_2$NR$^5$R$^6$, (CH$_2$)$_n$CH$_2$N$_3$, (CH$_2$)$_n$CH$_2$Hal, (CH$_2$)$_n$CH$_2$NO$_2$, (CH$_2$)$_n$CH$_2$SR$^{20}$, (CH$_2$)$_n$COSR$^{21}$ or (CH$_2$)$_n$-2,3,4,5-tetrazol-1-yl, wherein:

R is H or CO$_2$R forms a pharmaceutically acceptable salt or a pharmaceutically acceptable ester;

NR$^2$R$^3$ and NR$^5$R$^6$ are the same or different and comprise a free or functionally modified amino group, e.g., R$^2$, R$^3$, R$^5$ and R$^6$ are the same or different and are H, alkyl, cycloalkyl, aralkyl, aryl, OH, or alkoxy, with the proviso that at most only one of R$^2$ and R$^3$ are OH or alkoxy and at most only one of R$^5$ and R$^6$ are OH or alkoxy;

OR$^4$ comprises a free or functionally modified hydroxy group, e.g., R$^4$ is H, acyl; alkyl, cycloalkyl, aralkyl, or aryl;

Hal is F, Cl, Br or I;

SR$^{20}$ comprises a free or functionally modified thiol group;

R$^{21}$ is H or COSR$^{21}$ forms a pharmaceutically acceptable salt or a pharmaceutically acceptable thioester;

n is 0 or 2;

A, B, C and D is C$_1$–C$_5$ alkyl, alkenyl, or alkynyl or a C$_3$–C$_5$ allenyl group;

Y is

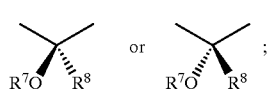

wherein R$^8$ is H or CH$_3$, and

X is CH$_2$, CH(CH$_3$) or C(CH$_3$)$_2$; or

Y is CH$_2$, CH(CH$_3$) or C(CH$_3$)$_2$, and X is

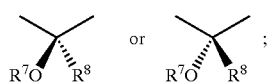

wherein R$^8$ is H or CH$_3$, with the proviso that Y cannot be CH$_2$ when X is

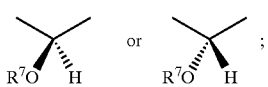

and

R⁷O comprises a free or functionally modified hydroxy group; and

XI:

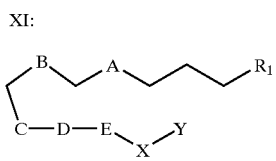

wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H or a pharmaceutically acceptable cation, or $CO_2R$ forms a pharmaceutically acceptable ester moiety;

$NR^2R^3$, $NR^5R^6$ are the same or different and comprise a free or functionally modified amino group;

$OR^4$ comprises a free or functionally modified hydroxy group;

Hal is F, Cl, Br, or I;

$SR^{20}$ comprises a free or functionally modified thiol group;

$R^{21}$ is H or a pharmaceutically acceptable cation, or $COSR^{21}$ forms a pharmaceutically acceptable thioester moiety;

A, B, C, D are the same or different and are $C_1$–$C_5$ alkyl, $C_2$–$C_5$ alkenyl, $C_{1-5}$ cyclopropyl, $C_2$–$C_5$ alkynyl, or a $C_3$–$C_5$ allenyl group;

E is

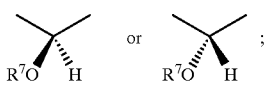

where $OR^7$ comprises a free or functionally modified hydroxy group;

$X=(CH_2)_m$ or $(CH_2)_mO$, where m=1–6; and

Y=a phenyl ring optionally substituted with alkyl, halo, trihalomethyl, acyl, or a free or functionally modified hydroxy, amino, or thiol group; or $X—Y=(CH_2)_pY^1$; where p=0–6; and $Y^1$ =

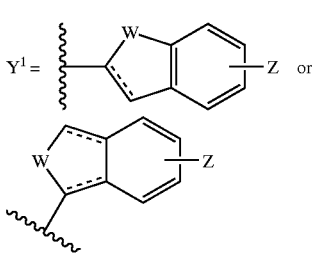

wherein:

$W=CH_2$, O, $S(O)_q$, $NR^8$, $CH_2CH_2$, $CH=CH$, $CH_2O$, $CH_2S(O)_q$, $CH=N$, or $CH_2NR^8$; where q=0–2, and $R^8=H$, alkyl, or acyl;

Z=H, alkyl, acyl, halo, trihalomethyl, or a free or functionally modified amino, thiol, or hydroxy group; and —— = single or double bond;

or X—Y=cyclohexyl.

2. The method of claim 1 wherein the HETE compound is a compound of formulas I–III.

3. The method of claim 1 wherein the HETE compound is a compound of formulas I–XI:

I–III:

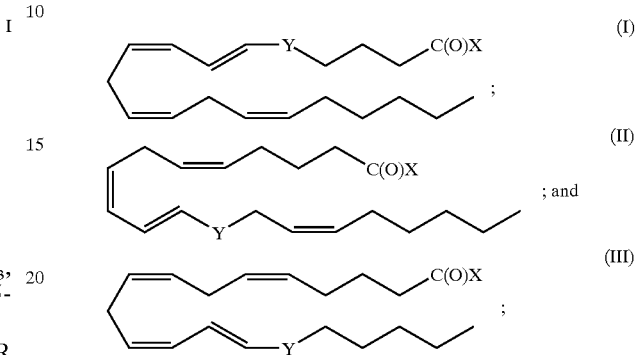

wherein:

X is $O^-M^+$, OR or NHR';

$M^+$ is $Na^+$, $K^+$, $Li^+$, or $Cs^+$;

R is H, or substituted or unsubstituted $C_{1-15}$ alkyl, cycloalkyl, (cycloalkyl)alkyl, aryl, or arylalkyl, wherein the substitution is made with a moiety selected from the group consisting of: $C_{1-6}$ alkyl, fluoro, chloro, bromo, iodo, OH, $OCH_2C(O)CH_3$, $OCH_2C(O)C_2H_5$, $OCH_3$, $OCH_2CH_3$, $OC(O)CH_3$, and $OC(O)C_2H_5$;

R' is H, or substituted or unsubstituted $C_{1-15}$ alkyl, cycloalkyl, (cycloalkyl)alkyl, aryl, or arylalkyl, wherein the substitution is made with a moiety selected from the group consisting of: $C_{1-6}$ alkyl, fluoro, chloro, bromo, iodo, OH, $OCH_2C(O)CH_3$, $OCH_2C(O)C_2H_5$, $OCH_3$, $OCH_2CH_3$, $OC(O)CH_3$, and $OC(O)C_2H_5$; and Y is

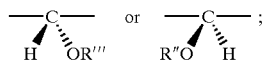

wherein R" is H or C(O)R;

IV:

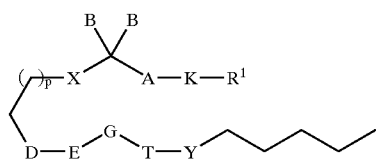

wherein:

$R^1$ is $CO_2R$, $CONR^2R^3$, $CH_2OR^4$, $CH_2NR^5R^6$, $CH_2N_3$, $CH_2$-Hal, $CH_2NO_2$, $CH_2SR^{20}$, $COSR^{21}$, or 2,3,4,5-tetrazol-1-yl, wherein:

R is H, $Na^+$, $K^+$, $Li^+$, $Cs^+$, $(A)_4N^+$, or $C_{1-15}$ alkyl, cycloalkyl, arylalkyl, aryl or alkoxy;

A is independently H or $C_{1-15}$ alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring;

$R^2$, $R^3$, $R^5$ and $R^6$ are the same or different and are H, OH, or $C_{1-15}$ alkyl, cycloalkyl, arylalkyl, aryl, or alkoxy, with the proviso that at most only one of $R^2$ and $R^3$ are OH or alkoxy and at most only one of $R^5$ and $R^6$ are OH or alkoxy;

$OR^4$ is OH, $OCH_2C(O)CH_3$, $OCH_2C(O)C_2H_5$, $OCH_3$, $OCH_2CH_3$, $OC(O)CH_3$, or $OC(O)C_2H_5$;

Hal is F, Cl, Br or I;

$SR^{20}$ is SH, $SC(O)CH_3$, $SCH_3$, $SC_2H_5$, $SCH_2C(O)C_2H_5$, and $SCH_2C(O)CH_3$;

$R^{21}$ is H or $C_{1-15}$ alkyl or aryl;

K is $C_2$–$C_8$ alkyl, alkenyl, or alkynyl, or a $C_3$–$C_8$ allenyl group;

A and X are the same or different and are a direct bond, $CH_2$, $NR^7$, O, or S, with the proviso that at least one of A and X is $NR^7$, O, or S;

B is H, or BB together comprises a double bonded O, S, or $NR^8$, with the proviso that BB comprises a double bonded O, S, or $NR^8$ when A and X are the same or different and are $NR^7$, O, or S; wherein:

$R^7$ and $R^8$ are the same or different and are H, OH, or $C_{1-15}$ alkyl, cycloalkyl, aryl, aralkyl, acyl, or alkoxy;

p is 0 or 1;

D-E, G-H are the same or different and are $CH_2CH_2$, CH=CH, or C≡C; and

Y is C(O) or

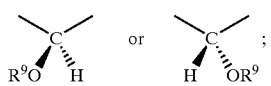

wherein $OR^9$ is OH, $OCH_2C(O)CH_3$, $OCH_2C(O)C_2H_5$, $OCH_3$, $OCH_2CH_3$, $OC(O)CH_3$, or $OC(O)C_2H_5$;

V:

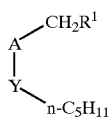

wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H, $Na^+$, $K^+$, $Li^+$, $Cs^+$, $(A)_4N^+$, or $C_{1-15}$ alkyl, cycloalkyl, arylalkyl, aryl or alkoxy;

A is independently H or $C_{1-15}$ alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring;

$R^2$, $R^3$, $R^5$ and $R^6$ are the same or different and are H, OH, or $C_{1-15}$ alkyl, cycloalkyl, arylalkyl, aryl, or alkoxy, with the proviso that at most only one of $R^2$ and $R^3$ are OH or alkoxy and at most only one of $R^5$ and $R^6$ are OH or alkoxy;

$OR^4$ is OH, $OCH_2C(O)CH_3$, $OCH_2C(O)C_2H_5$, $OCH_3$, $OCH_2CH_3$, $OC(O)CH_3$, or $OC(O)C_2H_5$;

Hal is F, Cl, Br, or I;

$R^{20}$ is H or $C_{1-15}$ alkyl or acyl;

$R^{21}$ is H or $C_{1-15}$ alkyl or aryl;

A is $L_1$-$A_1$-$L_2$, $L_1$-$A_2$-$L_2$, $L_3$-$A_2$-$L_4$, or $L_5$-$A_2$—$L_3$;

$A_1$ is $CH_2CH_2$;

$A_2$ is

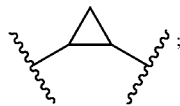

$L_1$ is $CH_2$-B-D;

B and D are the same or different and are $CH_2CH_2$, CH=CH, or C≡C;

$L_2$ is $CH_2$-K-$CH_2CH_2$;

K is $CH_2CH_2$, CH=CH, or C≡C;

$L_3$ is $CH_2CH_2CH_2$, $CH_2CH$=CH, $CH_2C$≡C, CH=$CHCH_2$, C≡$CCH_2$, or CH=C=CH;

$L_4$ is X—$CH_2CH_2$;

X is $CH_2CH_2CH$=CH, $CH_2CH_2C$≡C, $CH_2CH_2CH_2CH_2$, $CH_2CH$=$CHCH_2$, $CH_2C$≡$CCH_2$, CH=$CHCH_2CH_2$, C≡$CCH_2CH_2$, $CH_2CH$=C=CH, or CH=C=$CHCH_2$;

$L_5$ is $CH_2CH_2$-B-D; and

Y is C(O) or

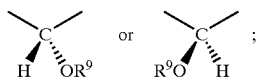

wherein $OR^9$ is OH, $OCH_2C(O)CH_3$, $OCH_2C(O)C_2H_5$, $OCH_3$, $OCH_2CH_3$, $OC(O)CH_3$, or $OC(O)C_2H_5$;

VI:

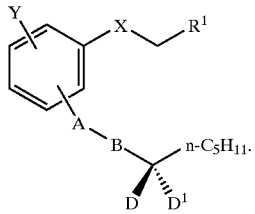

wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$ or 2,3,4,5-tetrazol-1-yl, wherein:

R is H, $Na^+$, $K^+$, $Li^+$, $Cs^+$, $(A)_4N^+$, or $C_{1-15}$ alkyl, cycloalkyl, arylalkyl, aryl or alkoxy;

A is independently H or $C_{1-15}$ alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring;

$R^2$, $R^3$, $R^5$ and $R^6$ are the same or different and are H, OH, or $C_{1-15}$ alkyl, cycloalkyl, arylalkyl, aryl, or alkoxy, with the proviso that at most only one of $R^2$ and $R^3$ are OH or alkoxy and at most only one of $R^5$ and $R^6$ are OH or alkoxy;

$OR^4$ is OH, $OCH_2C(O)CH_3$, $OCH_2C(O)C_2H_5$, $OCH_3$, $OCH_2CH_3$, $OC(O)CH_3$, or $OC(O)C_2H_5$;

Hal is F, Cl, Br or I;

$SR^{20}$ is SH, $SC(O)CH_3$, $SCH_3$, $SC_2H_5$, $SCH_2C(O)C_2H_5$, and $SCH_2C(O)CH_3$;

$R^{21}$ is H or $C_{1-15}$ alkyl or aryl;

X is $C_2$–$C_5$ alkyl, alkynyl, or alkenyl or a $C_3$–$C_5$ allenyl group;

Y is H, $OCH_2C(O)CH_3$, $OCH_2C(O)C_2H_5$, $OCH_3$, $OCH_2CH_3$, $OC(O)CH_3$, or $OC(O)C_2H_5$, Hal, $C(Hal)_3$,

NH$_2$, NHCH$_3$, NHC$_2$H$_5$, N(CH$_3$)$_2$, NHC(O)CH$_3$, NHOH, NH(OCH$_3$), SH, SC(O)CH$_3$, SCH$_3$, SC$_2$H$_5$, SCH$_2$C(O)C$_2$H$_5$, SCH$_2$C(O)CH$_3$, C(O)R$^7$, or C$_{1-5}$ alkyl;

R$^7$ is H, OH, or C$_{1-15}$ alkyl, alkoxy, amino, alkylamino or alkoxyamino;

A is a direct bond or C$_{1-3}$ alkyl;

B is CH$_2$CH$_2$, cis- or trans-CH=CH, or C≡C; and one of D and D$^1$ is H and the other is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$, or DD$^1$ together comprises a double bonded oxygen;

VII:

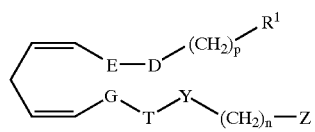

wherein:

R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$ or 2,3,4,5-tetrazol-1-yl, wherein:

R is H, Na$^+$, K$^+$, Li$^+$, Cs$^+$, (A)$_4$N$^+$, or C$_{1-15}$ alkyl, cycloalkyl, arylalkyl, aryl or alkoxy;

A is independently H or C$_{1-15}$ alkyl, cycloalkyl, (cycloalkyl)alkyl, alkyl(cycloalkyl), aryl, arylalkyl, heteroaryl, or (A)$_4$N$^+$ forms a heteroaryl, heterocycloalkenyl or heterocycloalkyl ring;

R$^2$, R$^3$, R$^5$ and R$^6$ are the same or different and are H, OH, or C$_{1-15}$ alkyl, cycloalkyl, arylalkyl, aryl, or alkoxy, with the proviso that at most only one of R$^2$ and R$^3$ are OH or alkoxy and at most only one of R$^5$ and R$^6$ are OH or alkoxy;

OR$^4$ is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$;

Hal is F, Cl, Br or I;

SR$^{20}$ is SH, SC(O)CH$_3$, SCH$_3$, SC$_2$H$_5$, SCH$_2$C(O)C$_2$H$_5$, and SCH$_2$C(O)CH$_3$;

R$^{21}$ is H or C$_{1-15}$ alkyl or aryl;

E-D is CH$_2$CH$_2$CH$_2$ or cis-CH$_2$CH=CH; or E is trans-CH=CH and D is CH(X) in either configuration, wherein X is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$; or E is CH$_2$CH$_2$ and D is a direct bond;

p is 1 or 3 when E-D is CH$_2$CH$_2$CH$_2$ or cis-CH$_2$CH=CH, or when E is trans-CH=CH and D is CH(X) in either configuration; or p is 0 when E is CH$_2$CH$_2$ and D is a direct bond;

G-T is CH$_2$CH$_2$, CH(SR$^7$)CH$_2$ or trans-CH=CH;

R$^7$ is H, or C$_{1-15}$ alkyl, aryl, aralkyl, cycloalkyl or acyl;

Y is CH(X) in either configuration, or C(O);

n is 0, 2 or 4; and

Z is CH$_3$, CO$_2$R, CONR$^2$R$^3$ or CH$_2$OR$^4$;

VIII:

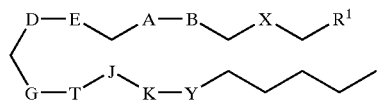

wherein:

R$^1$ is (CH$_2$)$_n$CO$_2$R, (CH$_2$)$_n$CONR$^2$R$^3$, (CH$_2$)$_n$CH$_2$OR$^4$, (CH$_2$)$_n$CH$_2$NR$^5$R$^6$, (CH$_2$)$_n$CH$_2$N$_3$, (CH$_2$)$_n$CH$_2$Hal, (CH$_2$)$_n$CH$_2$NO$_2$, (CH$_2$)$_n$CH$_2$SR$^{20}$, (CH$_2$)$_n$COSR$^{21}$ or (CH$_2$)$_n$-2,3,4,5-tetrazol-1-yl, wherein:

R is H, Na$^+$, K$^+$, Li$^+$, Cs$^+$, (A)$_4$N$^+$, or C$_{1-15}$ alkyl, cycloalkyl, arylalkyl, aryl or alkoxy;

A is independently H or C$_{1-15}$ alkyl, cycloalkyl, (cycloalkyl)alkyl, alkyl(cycloalkyl), aryl, arylalkyl, heteroaryl, or (A)$_4$N$^+$ forms a heteroaryl, heterocycloalkenyl or heterocycloalkyl ring;

R$^2$, R$^3$, R$^5$ and R$^6$ are the same or different and are H, OH, or C$_{1-15}$ alkyl, cycloalkyl, arylalkyl, aryl, or alkoxy, with the proviso that at most only one of R$^2$ and R$^3$ are OH or alkoxy and at most only one of R$^5$ and R$^6$ are OH or alkoxy;

OR$^4$ is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$;

Hal is F, Cl, Br or I;

SR$^{20}$ is SH, SC(O)CH$_3$, SCH$_3$, SC$_2$H$_5$, SCH$_2$C(O)C$_2$H$_5$, and SCH$_2$C(O)CH$_3$;

R$^{21}$ is H or C$_{1-15}$ alkyl or aryl;

n is 0 or 2;

X is O, S(O)$_p$, NR$^7$ or CH$_2$, with the proviso that X cannot be CH$_2$ when n is 0;

p is 0, 1 or 2;

R$^7$ is H, OH or C$_{1-15}$ alkyl, cycloalkyl, aralkyl, aryl, or alkoxy,

A-B, D-E, G-T and J-K are the same or different and are CH$_2$CH$_2$, CH=CH or C≡C, with the proviso that at least one of A-B, D-E, G-T and J-K must be CH=CH or C≡C; and Y is C(O), or

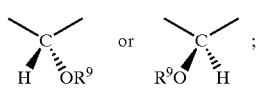

wherein OR$^9$ is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$;

IX:

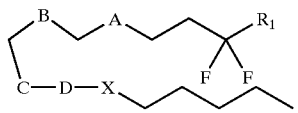

wherein:

R$^1$ is CO$_2$R, CONR$^2$R$^3$, CH$_2$OR$^4$, CH$_2$NR$^5$R$^6$, CH$_2$N$_3$, CH$_2$Hal, CH$_2$NO$_2$, CH$_2$SR$^{20}$, COSR$^{21}$ or 2,3,4,5-tetrazol-1-yl, wherein:

R is H, Na$^+$, K$^+$, Li$^+$, Cs$^+$, (A)$_4$N$^+$, or C$_{1-15}$ alkyl, cycloalkyl, arylalkyl, aryl or alkoxy;

A is independently H or C$_{1-15}$ alkyl, cycloalkyl, (cycloalkyl)alkyl, alkyl(cycloalkyl), aryl, arylalkyl, heteroaryl, or (A)$_4$N$^+$ forms a heteroaryl, heterocycloalkenyl or heterocycloalkyl ring;

R$^2$, R$^3$, R$^5$ and R$^6$ are the same or different and are H, OH, or C$_{1-15}$ alkyl, cycloalkyl, arylalkyl, aryl, or alkoxy, with the proviso that at most only one of R$^2$ and R$^3$ are OH or alkoxy and at most only one of R$^5$ and R$^6$ are OH or alkoxy;

OR$^4$ is OH, OCH$_2$C(O)CH$_3$, OCH$_2$C(O)C$_2$H$_5$, OCH$_3$, OCH$_2$CH$_3$, OC(O)CH$_3$, or OC(O)C$_2$H$_5$;

Hal is F, Cl, Br or I;

$SR^{20}$ is SH, $SC(O)CH_3$, $SCH_3$, $SC_2H_5$, $SCH_2C(O)C_2H_5$, and $SCH_2C(O)CH_3$;

$R^{21}$ is H or $C_{1-15}$ alkyl or aryl;

A, B, C and D are the same or different and are $C_1$–$C_5$ alkyl, alkenyl, or alkynyl or a $C_3$–$C_5$ allenyl group;

X is C(O) or

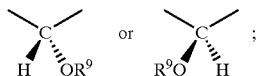

wherein $OR^9$ is OH, $OCH_2C(O)CH_3$, $OCH_2C(O)C_2H_5$, $OCH_3$, $OCH_2CH_3$, $OC(O)CH_3$, or $OC(O)C_2H_5$;

X:

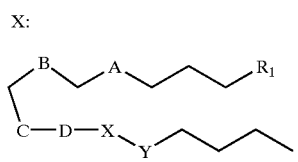

I wherein:

$R^1$ is $(CH_2)_nCO_2R$, $(CH_2)_nCONR^2R^3$, $(CH_2)_nCH_2OR^4$, $(CH_2)_nCH_2NR^5R^6$, $(CH_2)_nCH_2N_3$, $(CH_2)_nCH_2Hal$, $(CH_2)_nCH_2NO_2$, $(CH_2)_nCH_2SR^{20}$, $(CH_2)_n(COSR^{21}$ or $(CH_2)_n$-2,3,4,5-tetrazol-1-yl, wherein:

R is H, $Na^+$, $K^+$, $Li^+$, $Cs^+$, $(A)_4N^+$, or $C_{1-15}$ alkyl, cycloalkyl, arylalkyl, aryl or alkoxy;

A is independently H or $C_{1-15}$ alkyl, cycloalkyl, (cycloalkyl)alkyl, alkyl(cycloalkyl), aryl, arylalkyl, heteroaryl, or $(A)_4N^+$ forms a heteroaryl, heterocloalkenyl or heterocycloalkyl ring;

$R^2$, $R^3$, $R^5$ and $R^6$ are the same or different and are H, OH, or $C_{1-15}$ alkyl, cycloalkyl, arylalkyl, aryl, or alkoxy, with the proviso that at most only one of $R^2$ and $R^3$ are OH or alkoxy and at most only one of $R^5$ and $R^6$ are OH or alkoxy;

$OR^4$ is OH, $OCH_2C(O)CH_3$, $OCH_2C(O)C_2H_5$, $OCH_3$, $OCH_2CH_3$, $OC(O)CH_3$, or $OC(O)C_2H_5$;

Hal is F, Cl, Br or I;

$SR^{20}$ is SH, $SC(O)CH_3$, $SCH_3$, $SC_2H_5$, $SCH_2C(O)C_2H_5$, and $SCH_2C(O)CH_3$;

$R^{21}$ is H or $C_{1-15}$ alkyl or aryl;

n is 0 or 2;

A, B, C and D is $C_1$–$C_5$ alkyl, alkenyl, or alkynyl or a $C_3$–$C_5$ allenyl group;

Y is

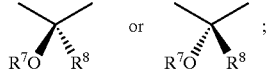

wherein $R^8$ is H or $CH_3$, and

X is $CH_2$, $CH(CH_3)$ or $C(CH_3)_2$; or

Y is $CH_2$, $CH(CH_3)$ or $C(CH_3)_2$, and X is

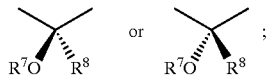

wherein $R^8$ is H or $CH_3$, with the proviso that Y cannot be $CH_2$ when X is

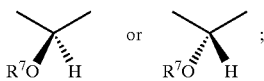

and $R^7O$ is OH, $OCH_2C(O)CH_3$, $OCH_2C(O)C_2H_5$, $OCH_3$, $OCH_2CH_3$, $OC(O)CH_3$, or $OC(O)C_2H_5$; and

XI:

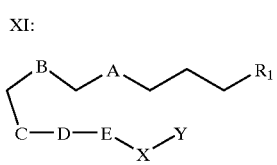

I wherein:

$R^1$ is $CO_2R$, $CONR^2R^3$, $CH_2OR^4$, $CH_2NR^5R^6$, $CH_2N_3$, $CH_2Hal$, $CH_2NO_2$, $CH_2SR^{20}$, $COSR^{21}$, or 2,3,4,5-tetrazol-1-yl, where:

R is H, $Na^+$, $K^+$, $Li^+$, $Cs^+$, $(A)_4N^+$, or $C_{1-15}$ alkyl, cycloalkyl, arylalkyl, aryl or alkoxy;

A is independently H or $C_{1-15}$ alkyl, cycloalkyl, (cycloalkyl)alkyl, alkyl(cycloalkyl), aryl, arylalkyl, heteroaryl, or $(A)_4N^+$ forms a heteroaryl, heterocloalkenyl or heterocycloalkyl ring;

$R^2$, $R^3$, $R^5$ and $R^6$ are the same or different and are H, OH, or $C_{1-15}$ alkyl, cycloalkyl, arylalkyl, aryl, or alkoxy, with the proviso that at most only one of $R^2$ and $R^3$ are OH or alkoxy and at most only one of $R^5$ and $R^6$ are OH or alkoxy;

$OR^4$ is OH, $OCH_2C(O)CH_3$, $OCH_2C(O)C_2H_5$, $OCH_3$, $OCH_2CH_3$, $OC(O)CH_3$, or $OC(O)C_2H_5$;

Hal is F, Cl, Br or I;

$SR^{20}$ is SH, $SC(O)CH_3$, $SCH_3$, $SC_2H_5$, $SCH_2C(O)C_2H_5$, and $SCH_2C(O)CH_3$;

$R^{21}$ is H or $C_{-1-15}$ alkyl or aryl;

A, B, C, D are the same or different and are $C_1$–$C_5$ alkyl, $C_2$–$C_5$ alkenyl, $C_{1-5}$ cyclopropyl, $C_2$–$C_5$ alkynyl, or a $C_3$–$C_5$ allenyl group;

E is

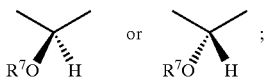

where $OR^7$ is OH, $OCH_2C(O)CH_3$, $OCH_2C(O)C_2H_5$, $OCH_3$, $OCH_2CH_3$, $OC(O)CH_3$, or $OC(O)C_2H_5$;

X=$(CH_2)_m$ or $(CH_2)_mO$, where m=1–6; and

Y=a phenyl ring optionally substituted with $C_{1-6}$ alkyl or acyl, Hal, $C(Hal)_3$, OH, $OCH_2C(O)CH_3$, $OCH_2C(O)C_2H_5$, $OCH_3$, $OCH_2CH_3$, $OC(O)CH_3$, $OC(O)C_2H_5$, $NH_2$, $NHCH_3$, $NHC_2H_5$, $N(CH_3)_2$, $NHC(O)CH_3$, NHOH, NH(OCH$_3$), SH, SC(O)CH$_3$, SCH$_3$, SC$_2$H$_5$, SCH$_2$C(O)C$_2$H$_5$, or SCH$_2$C(O)CH$_3$; and X—Y=(CH$_2$)$_p$Y$^1$; where p=0–6; and Y$^1$ = 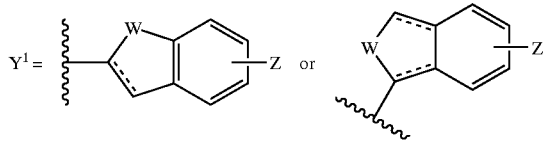

wherein:

W=CH$_2$, O, S(O)$_q$, NR$^8$, CH$_2$CH$_2$, CH=CH, CH$_2$O, CH$_2$S(O)$_q$, CH=N, or CH$_2$NR$^8$; where q=0–2, and R$^8$=H, or C$_{1-15}$ alkyl or acyl;

Z=H, C$_{1-15}$ alkyl or acyl, Hal, C(Hal)$_3$, OH, OCH$_2$C(O)CH$_3$, OCH$_2$C(O)C$_2$H$_5$, OCH$_3$, OCH$_2$CH$_3$, OC(O)CH$_3$, OC(O)C$_2$H$_5$, NH$_2$, NHCH$_3$, NHC$_2$H$_5$, N(CH$_3$)$_2$, NHC(O)CH$_3$, NHOH, NH(OCH$_3$), SH, SC(O)CH$_3$, SCH$_3$, SC$_2$H$_5$, SCH$_2$C(O)C$_2$H$_5$, or SCH$_2$C(O)CH$_3$; and ———=single or double bond;

or X—Y=cyclohexyl.

4. The method of claim 1 wherein the HETE compound is present in the composition in a concentration range of about 0.000001 to 10% w/v.

5. The method of claim 4 wherein the HETE compound is present in the composition in a concentration range of about 0.00001–0.01% w/v.

\* \* \* \* \*